US00PP17117P2

(12) United States Plant Patent
Sanders

(10) Patent No.: US PP17,117 P2
(45) Date of Patent: Sep. 26, 2006

(54) ***AGERATUM* PLANT NAMED 'AGALIB'**

(50) Latin Name: *Ageratum houstonianum*
Varietal Denomination: Agalib

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 1 day.

(21) Appl. No.: 11/206,428

(22) Filed: Aug. 18, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Bruce Vrana

(57) ABSTRACT

A new *Ageratum* plant, characterized particularly as to novelty by large light violet blue flowers, early flowering, freely branching plant habit and vigorous growth.

1 Drawing Sheet

Latin name of the genus and species of the plant claimed: *Ageratum houstonianum.*

Varietal denomination: 'Agalib'.

BACKGROUND OF THE NEW PLANT

The present invention comprises a new distinct cultivar of *Ageratum*, botanically known as *Ageratum houstonianum*. The new cultivar is propagated from cuttings resulting from the cross in October 1999 of 'U 43-2' as female parent and 'T393-3' as male parent. 'U 43-2' is not commercially available and has not been patented. 'T393-3' is not commercially available and has not been patented.

As a result of this cross, present cultivar was created in August 2000 in Enkhuizen, Netherlands and has been repeatedly asexually reproduced by cuttings in Enkhuizen, Netherlands, in Gilroy, Calif., and in Sarrians, France over a three-year period. The distinctive characteristics of this new *Ageratum* are stable and reproduced true to type in successive generations of asexual reproduction. It takes 8 to 10 weeks to produce a finished plant, depending on the temperature.

This new *Ageratum* plant is an annual in most climatical zones in the U.S., only in zones 9 and 10 it is a perennial plant.

SUMMARY OF THE INVENTION

The following traits have been repeatedly observed and are determined to be the unique characterists of 'Agalib'. These characteristics in combination distinguish 'Agalib' as a new and distinct *Ageratum* cultivar:

1. Vigorous, upright and mounded growth habit.
2. Freely branching habit.
3. Freely flowering habit with large capitula in compound umbels.
4. Light violet blue capitula on green coloured leaves.

Plants of the new *Ageratum* differ primarily from the plants of the female parent selection in the following characteristics:

Plants of the new *Ageratum* have light violet blue coloured capitula whereas plants of the female parent selection have white and blue capitula. Plants of the new *Ageratum* have a good branching habit, whereas the plants of the female parent have a less branching habit.

Plants of the new *Ageratum* differ primarily from the male plant selection in the following characteristics:

Plants of the new *Ageratum* have light violet blue coloured capitula whereas plants of the male parent selection have white capitula. Plants of the new *Ageratum* have a vigorous habit with large leaves, whereas the plants of the male parent have a compact habit.

DESCRIPTION OF THE DRAWING

This new *Ageratum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Ageratum*. The data which defines these characteristics were collected from asexual reproductions carried out in Enkhuizen, Netherlands. The plant history was taken on 20 weeks old plants, blossomed under natural light in the field.

Color readings were taken in the greenhouse under ambient light. Color references are primarily to The R.H.S. Colour Chart of The Royal Horticultural Society of London.

TABLE 1

Differences between the new cultivar 'Agalib' and similar cultivars

| | 'Agalib' | 'Agetis' (P.P. 15,627) | 'Agapel' |
|---|---|---|---|
| Flower color | Light violet blue | Violet blue | Near white |
| Size of capitulum | 16–22 mm | 16–21 mm | 16–22 mm |
| Plant height | 20–27 cm | 20–25 cm | 20–25 cm |
| Diameter of plant | 32–48 cm | 35–40 cm | 32–40 cm |

The plant:

*Classification.*—Botanical: *Ageratum houstonianum.*

*Parentage.*—Female parent: Proprietary *Ageratum houstonianum* selection identified as code number 'U 43-2,' not patented. Pollen parent: Proprietary *Ageratum houstonianum* selection identified as code number 'T393-3,' not patented.

*Growth habit.*—Ascending, well branched.

*Plant height.*—20–27 cm.

*Spreading area of plant.*—32–48 cm.

*Growth rate.*—Vigorous.

*Strength.*—Very good.

*Branching character.*—Freely branching and lateral branching at every node.

*Blooming period.*—Year round.

The stem:

*Stem length.*—5–22 cm.

*Diameter.*—4–7 mm.

*Shape.*—Round.

*Color.*—RHS 146D.

*Anthocyan pigmentation.*—A little bit on the stems.

*Length of internode.*—20–70 mm, depending on the light where the plant is propagated.

*Pubescence.*—Slightly pubescent.

The foliage:

*Phyllotaxis.*—Opposite, decussate and alternate.

*Shape of blade.*—Cordate.

*Texture.*—Upper side: Slightly pubescent. Lower side: Slightly pubescent.

*Venation.*—Reticulate.

*Leaf margin.*—Serrate.

*Leaf base.*—Subcordate.

*Leaf apex.*—Acute.

*Length.*—3–6 mm.

*Width.*—3–5.5 mm.

*Colour.*—Upper side: Dark green RHS 137A. Lower side: Medium green RHS 137C.

*Pubescence.*—Some pubescence is present.

*Length of petiole.*—1.2–3.0 mm.

*Diameter of petiole.*—1–3 mm.

*Color of petiole.*—RHS 146C Light green.

*Petiole surface texture.*—Slightly pubescent.

Inflorescence:

*Inflorescence.*—Compound umbel of capitula.

*Number of inflorescence per plant.*—70–90.

*Umbel size.*—3.5–6 cm.

*Umbel depth.*—2–4 cm.

*Length of peduncle.*—5–20 mm.

*Diameter of peduncle.*—1–3 mm.

*Color of peduncle.*—RHS 137B.

*Length of pedicel.*—5–25 mm.

*Diameter of pedicel.*—1–2 mm.

*Color of pedicel.*—RHS 137D.

*Number of capitula per inflorescence.*—10–20.

*Number of disc florets per capitulum.*—50–85.

*Capitulum in bud stage.*—Round, flat capitulum, showing unopened florets from the start.

*Number of ray florets.*—0.

*Shape of the corolla of the disk floret.*—Actinomorphic.

*Number of lobes.*—5.

*Length of disk floret.*—3–4 mm.

*Diameter of disk floret.*—1 mm.

*Color of disk floret upper side.*—RHS 91D with tip RHS 72A.

*Color of disk floret lower side.*—RHS 154B.

*Number of phyllaries per capitulum.*—25–35.

*Length of phyllaries.*—4–6 mm.

*Diameter of phyllaries.*—0.5–1.5 mm.

*Color of phyllaries.*—Upper side: RHS 137B with tip RHS 72A. Inner side: RHS 137C with tip RHS 72A.

*Diameter of capitulum at beginning of flowering.*—6–10 mm.

*Depth of capitulum.*—5–10 mm.

*Color of capitulum at beginning of flowering.*—RHS 88D.

*Diameter of capitulum at full flowering.*—16–22 mm.

*Color of capitulum at full flowering.*—RHS 92B.

Reproductive organs:

*Number of pistils.*—1.

*Shape of pistils.*—Style with two filiform branches.

*Length of stigma and style.*—7–9 mm.

*Color of stigma.*—RHS 94B.

*Inferior ovary.*—5 ribbed.

*Pappus.*—Short.

*Number of anthers.*—5, connate in a tube, filaments free.

*Shape of anthers.*—Calcarate.

*Pollen.*—A little pollen is present.

*Color of pollen.*—RHS 155B.

*Fragrance.*—No fragrance.

*Lastingness of the bloom.*—The capitula of one umbel open over a period of 3 to 4 weeks.

*Seedset.*—No seedset.

Roots:

*Type of roots.*—Fibrous. Roots start to grow on every part of the stem that contacts the soil, so not only at the nodes.

Physiological and ecological characteristics: Good tolerance to heat and cold, but no frost tolerance. Strong resistance to pests and diseases.

What is claimed is:

1. A new and distinct cultivar of *Ageratum houstonianum* plant named 'Agalib,' as substantially illustrated and described herein.

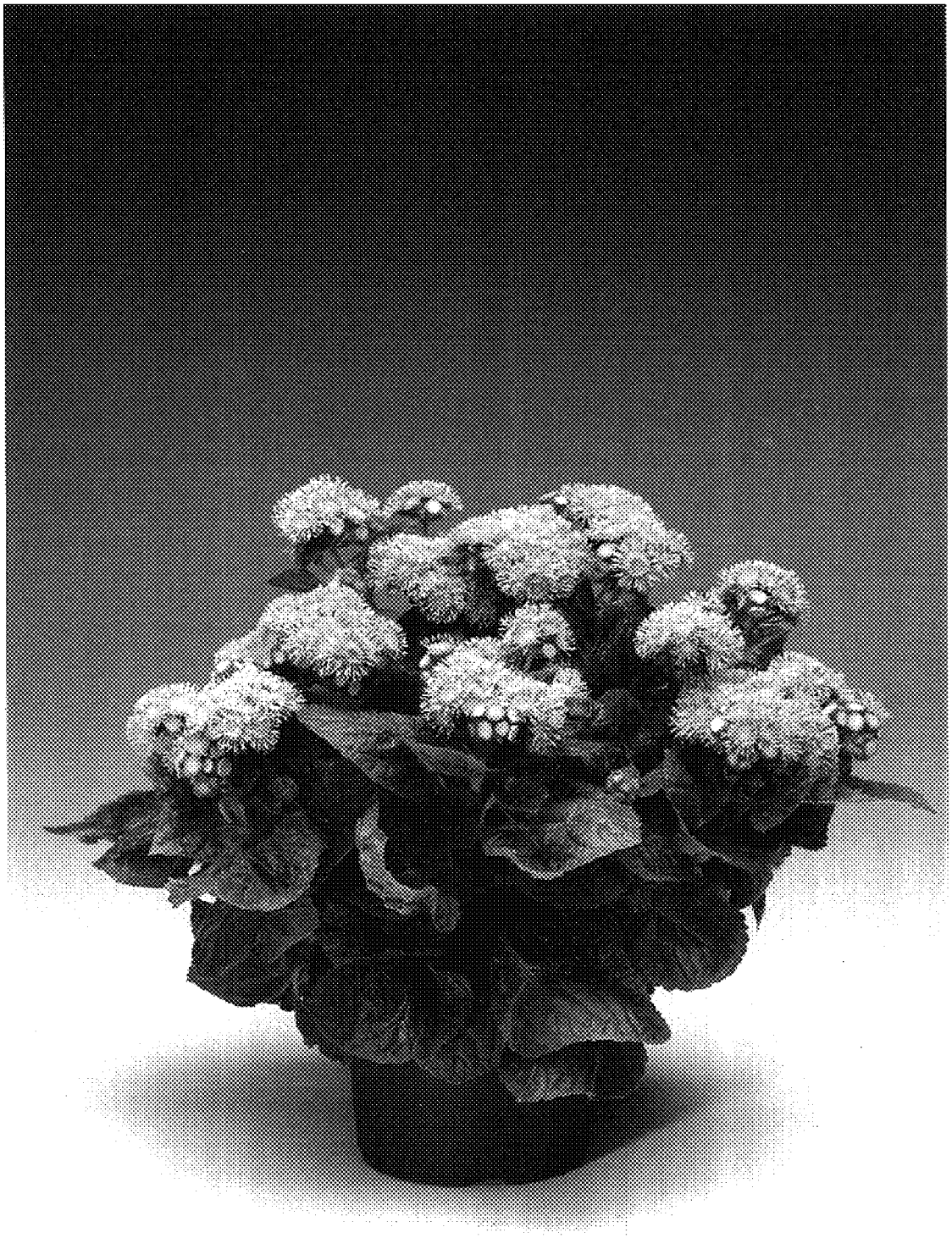

* * * * *